(12) United States Patent
Kiefl et al.

(10) Patent No.: US 12,324,451 B2
(45) Date of Patent: Jun. 10, 2025

(54) PRODUCTION OF ETHANOL-FREE VANILLA EXTRACTS

(71) Applicant: SYMRISE AG, Holzminden (DE)

(72) Inventors: Johannes Kiefl, Holzminden (DE); Stefan Brennecke, Halle (DE); Martin Heinemeyer, Höxter (DE); Dominik Winkler, Höxter (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 18/141,249

(22) Filed: Apr. 28, 2023

(65) Prior Publication Data

US 2023/0263202 A1 Aug. 24, 2023

Related U.S. Application Data

(62) Division of application No. 16/980,270, filed as application No. PCT/EP2018/056304 on Mar. 13, 2018, now Pat. No. 11,672,266.

(51) Int. Cl.
*A23L 27/10* (2016.01)
*A61K 8/9794* (2017.01)
*A61K 36/898* (2006.01)

(52) U.S. Cl.
CPC .............. *A23L 27/11* (2016.08); *A23L 27/115* (2016.08); *A61K 8/9794* (2017.08); *A61K 36/898* (2013.01); *A23V 2002/00* (2013.01); *A61K 2236/15* (2013.01); *A61K 2236/333* (2013.01); *A61K 2236/55* (2013.01)

(58) Field of Classification Search
CPC ........ A23L 27/11; A23L 27/115; A23L 27/10; A61K 8/9794; A61K 36/898; A61K 2236/15; A61K 2236/333; A61K 2236/55; A23V 2002/00

See application file for complete search history.

(56) References Cited

U.S. PATENT DOCUMENTS

| 2,835,591 A | 5/1958 | Graves et al. |
| 2007/0071710 A1 | 3/2007 | Maestro et al. |

FOREIGN PATENT DOCUMENTS

| DE | 31 37 230 A1 | 4/1983 |
| DE | 4027227 C2 | 4/1997 |
| EP | 1 928 447 B1 | 2/2016 |
| JP | 4-214799 A | 8/1992 |
| WO | WO-2006/047404 A2 | 5/2006 |

OTHER PUBLICATIONS

Kerala Agricultural University (http://www.celkau.in/crops/spices/Vanilla/vanilla_composition_and_vanillin_content.aspx) retrieved on Aug. 28, 2024, 2 pages. (Year: 2013).*
Wayback Machine date-capture recording of Kerala Agricultural University 2013, (https://web.archive.org/web/20240000000000*/http://www.celkau.in/crops/spices/Vanilla/vanilla_composition_and_vanillin_content.aspx) retrieved on Aug. 28, 2024, 1 page. (Year: 2024).*
JPH08168355A translated document, 6 pages. (Year: 2012).*
Office Action (and English translation) from European Application No. 18 712 136.3 dated Apr. 17, 2024.
Fei et al., "Optimization of Refining and Volatile Composition Analysis of Vanilla Extract," Food Science, 39(39):188-193 (2018).
International Search Report and Written Opinion for Application No. PCT/EP2018/056304, dated Dec. 10, 2018.
Jadhav et al., "Extraction of Vanillin form Vanilla Pods: a comparison Study of Conventional Soxhlet and Ultrasound Assisted Extraction," Journal of Food Engineering, 93(4):421-426 (2009).
JPH08168355A translated doc (Year: 1996).
Lavine, "Analysis of vanilla extract by reversed phase liquid chromatography uisng water rich mobile phases," Microchemical Journal 103:49-61 (2012).
Office Action and English Translation from Indonesian Patent Application No. P00202008916 dated Sep. 30, 2022.
Pérez-Silva et al., "GC-MS and GC-olfactometry analysis of aroma compounds in a representative organic aroma extract from cured vanilla ( *Vanilla planifolia* G. Jackson) beans," Food Chemistry 99:728-735 (2006).
Ranadive, "Vanillin and Related Flavor Compounds in Vanilla Extracts Made from Beans of Various Global Origins," Journal of Agricultural and Food Chemistry, 40:1922-1924 (1992).
Schwarz et al., "Identification of Novel Orosensory Active Molecules in Cured Vanilla Beans (Vanilla planifolia)," J. Agric. Food Chem., 57:3729-3737 (2009).
Schwarz et al., "Identification of Novel Orosensory Active Molecules in Cured Vanilla Beans (Vanilla planifolia)," Jounral of Agricultural and Food Chemistry, 57(9):3729-3737 (2009).

* cited by examiner

*Primary Examiner* — J. E. Angell
*Assistant Examiner* — Jacob A Boeckelman
(74) *Attorney, Agent, or Firm* — MARSHALL, GERSTEIN & BORUN LLP

(57) ABSTRACT

The present invention relates to a process for producing an ethanol-free vanilla extract, and an ethanol-free vanilla extract obtainable by the process according to the invention. In particular, the present invention relates to an ethanol-free vanilla extract comprising at most 100 mg/kg ethanol, the use of this ethanol-free vanilla extract and products comprising the ethanol-free vanilla extract. The focus of the present invention is in particular to provide an ethanol-free vanilla extract which contains only traces of ethanol naturally contained in fermented vanilla beans and is produced without the use of ethanol.

19 Claims, 5 Drawing Sheets

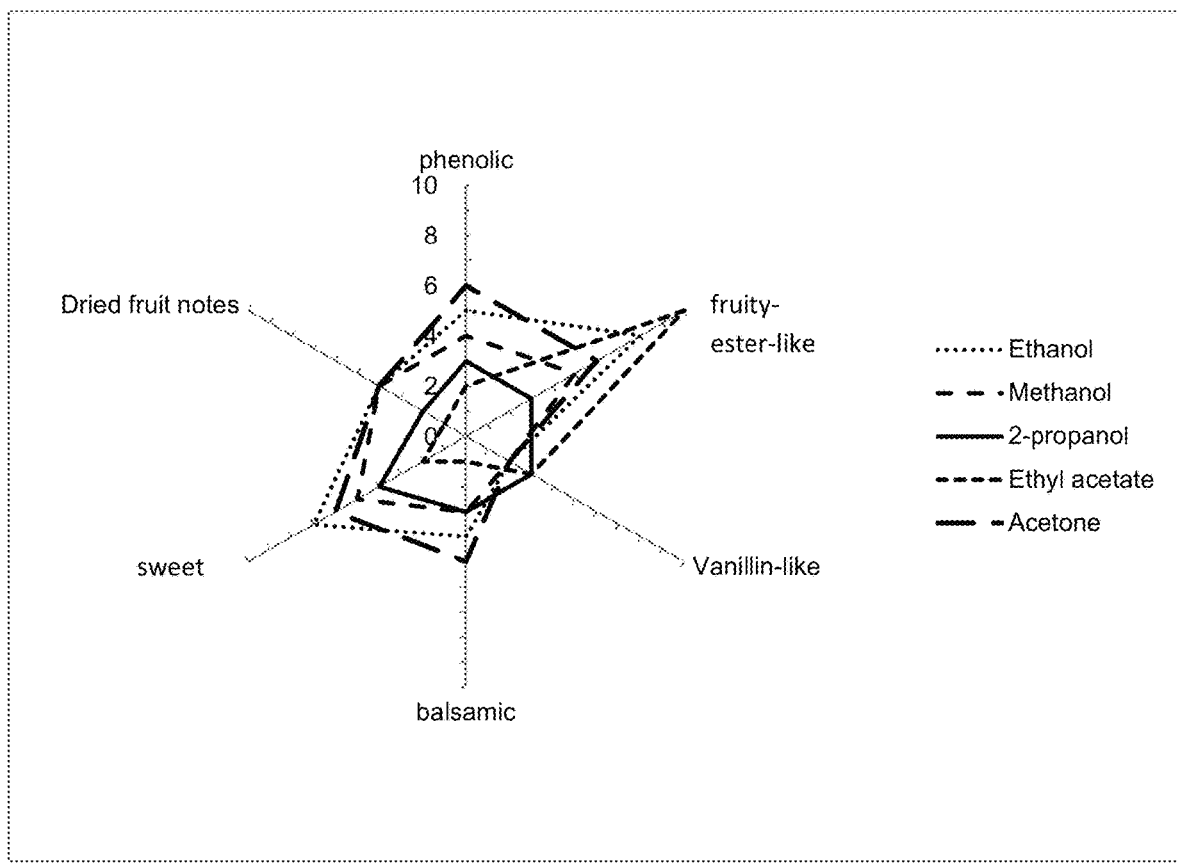
Figure 1: Sensory profiles of extracts of fermented vanilla beans using the method according to the invention

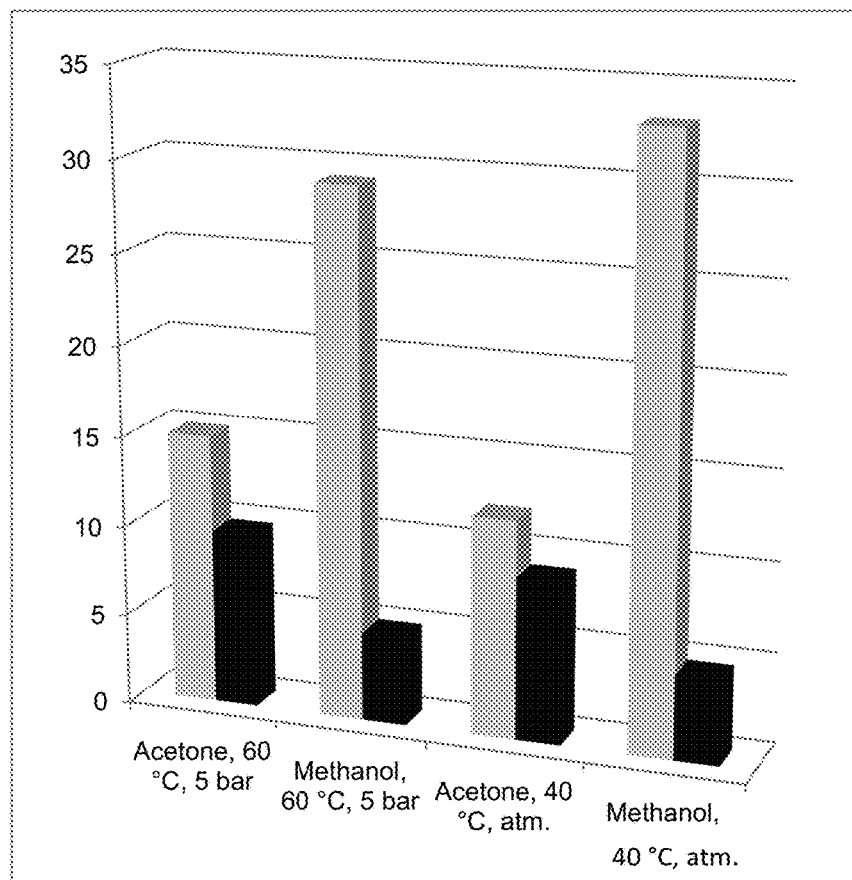
Figure 2: Vanillin contents (black bars, expressed as a percentage) and soluble extract contents (grey bars, expressed as a percentage) of acetone and methanol extracts of fermented vanilla beans according to the method of the invention

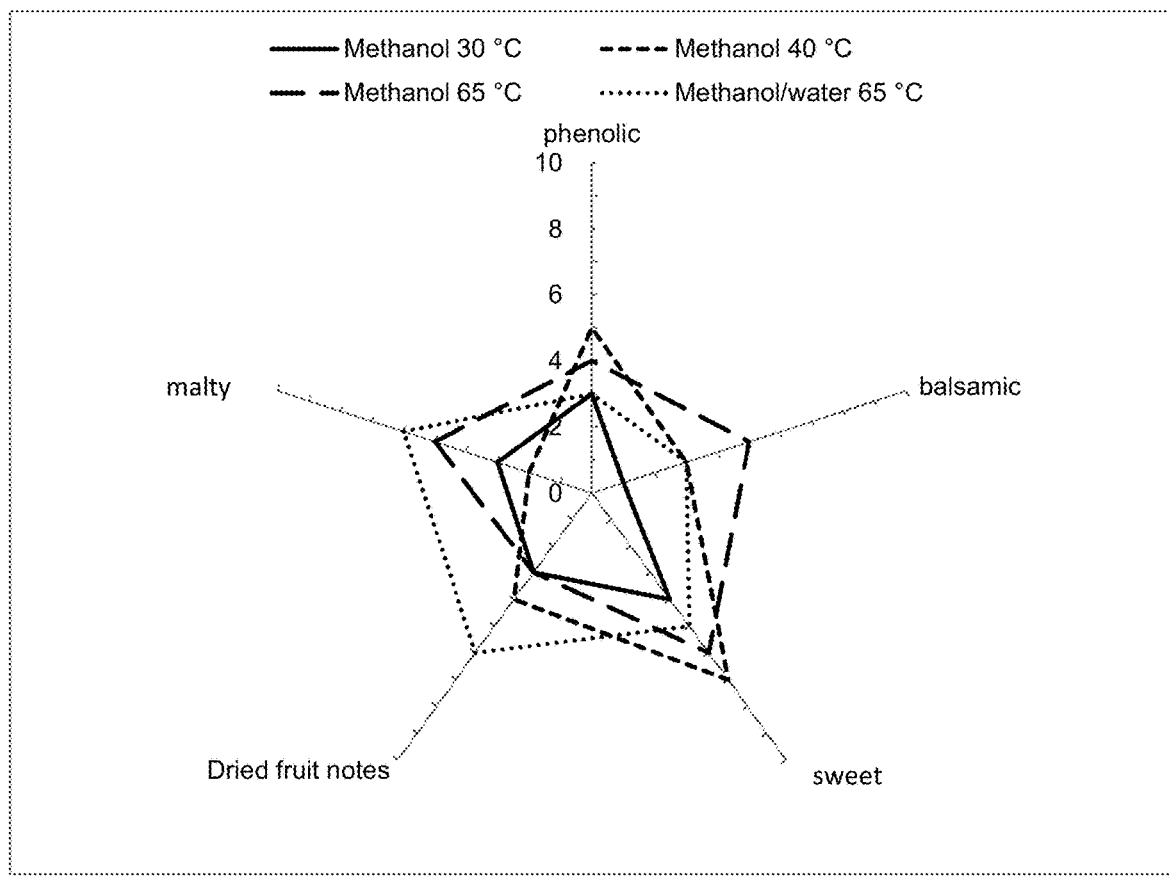
Figure 3: Sensory profiles of extracts of fermented vanilla beans as a function of extraction temperature

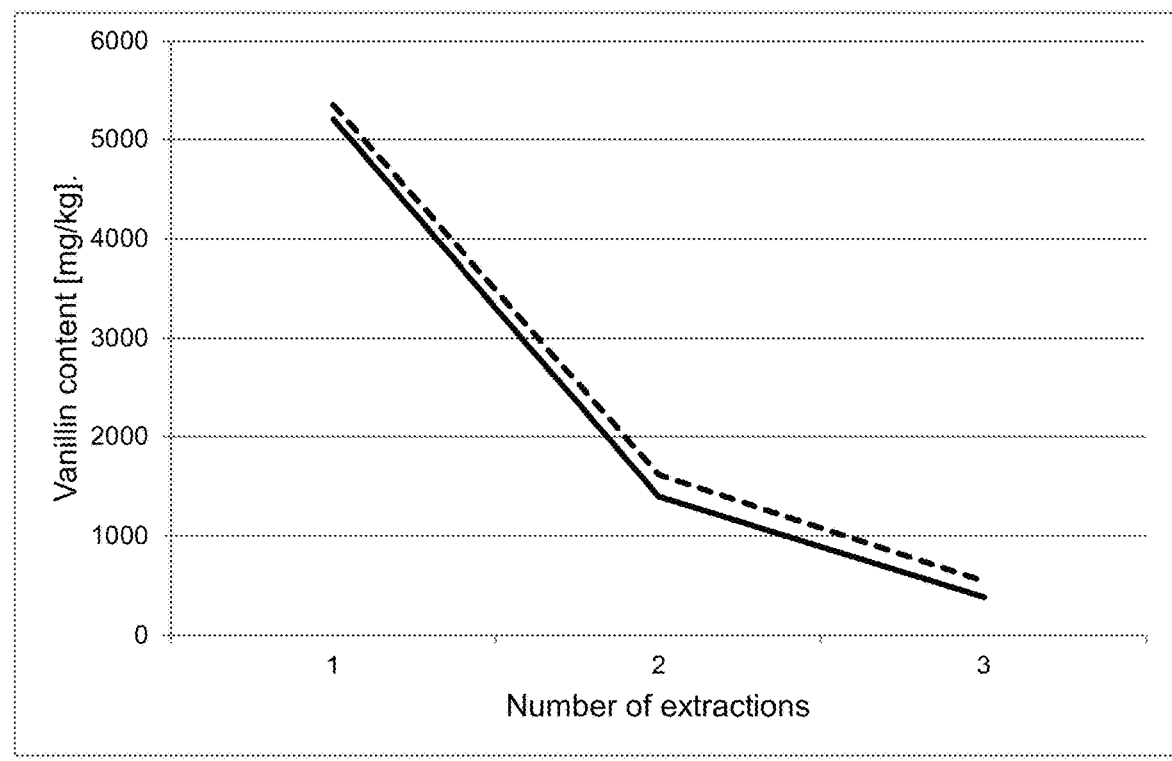
Figure 4: Vanillin yields in a consecutive extraction with acetone and methanol. The solid line describes the vanillin contents of an extraction with acetone, the dashed line describes the vanillin contents of an extraction with methanol.

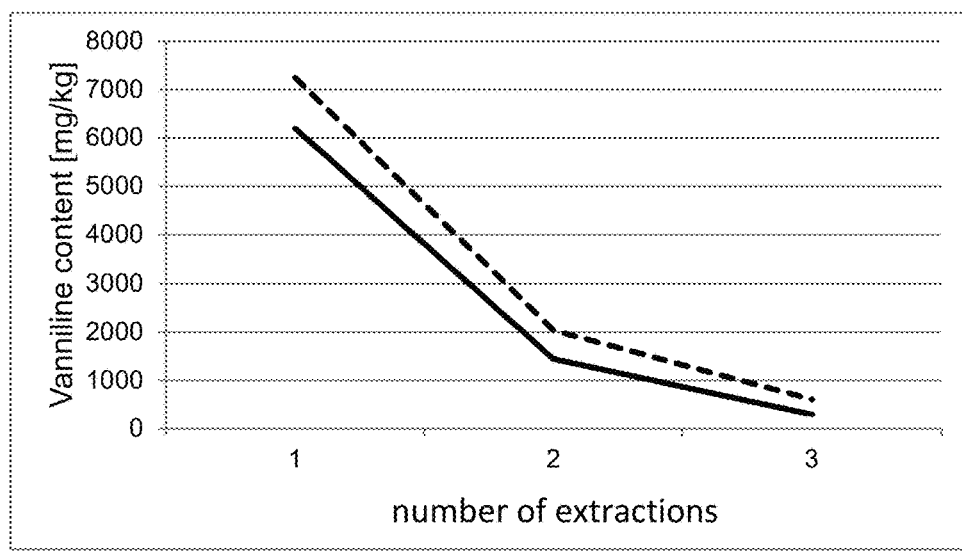
Figure 5: Vanillin yields in a consecutive extraction with methanol at different temperatures. The solid line describes the vanillin content of an extraction at 25 °C, the dotted line describes the vanillin content of an extraction at 65 °C.

PRODUCTION OF ETHANOL-FREE VANILLA EXTRACTS

CROSS-REFERENCE TO RELATED APPLICATIONS

This is a divisional of U.S. application Ser. No. 16/980,270, filed Sep. 11, 2020 which is a U.S. National Phase of International Application No. PCT/EP2018/056304, filed Mar. 13, 2018, the contents of which are incorporated herein by reference.

FIELD OF THE INVENTION

The present invention relates to a process for producing an ethanol-free vanilla extract, an ethanol-free vanilla extract obtainable by the process according to the invention, an ethanol-free vanilla extract comprising at most 100 mg/kg ethanol, the use of the ethanol-free vanilla extract, and products comprising the ethanol-free vanilla extract. The focus of the present invention is in particular to provide a process for the production of an ethanol-free vanilla extract without the use of ethanol and to provide an ethanol-free vanilla extract having only traces of ethanol naturally contained in fermented vanilla beans and produced without the use of ethanol.

STATE OF THE ART

Vanilla is a spice obtained from the fermented capsule fruits of various species of the orchid genus Vanilla. Besides the spice vanilla (*Vanilla planifolia*), the Tahiti vanilla (*Vanilla tahitensis*) and the Guadeloupe vanilla (*Vanilla pompona*) are of commercial importance.

The aroma of the dried and fermented pods of *Vanilla planifolia, Vanilla tahitensis* and *Vanilla pompona* is one of the highest quality and most widely used aromas worldwide. It is used for the flavouring of numerous foodstuffs such as ice cream, dairy products, desserts, chocolate products, bakery products, spirits, etc. In addition to other flavoring substances, vanilla beans contain on average about 1.6 to 2.4% of the flavoring substance vanillin, which makes an important contribution to the flavor impression.

Extracts from the above vanilla beans are preferred to vanillin-based extract-free flavours, especially because of their complex and authentic taste profile.

Fermented vanilla beans have been extracted with ethanol as extraction solvent for decades. The resulting extract is then concentrated by distillation. During this process, process and storage-related changes in the sensory profile occur.

The olfactory impression of vanilla extracts is caused by more than 30 odorous substances, such as capric acid, methyl cinnamate, guaiacol, 4-methyl guaiacol, ethyllinolenate, p-hydroxybenzoic acid, p-hydroxybenzaldehyde and vanillin (Pérez-Silva et al., Food Chemistry 99, 2006, 728-735).

The taste impression of vanilla extracts is caused by numerous non-volatile substances. For example, Schwarz and Hofmann et al. were able to detect more than 10 flavouring substances such as 4-(4-hydroxybenzyl)-2-methoxyphenol, divanillin, (1-O-vanilloyl)-(6-O-feruloyl)-β-D-glucopyranoside, whereby many sensory active substances are still unknown (Schwarz and Hofmann, J. Agric. Food Chem., 57, 2009, 3729-3737).

Since the above-mentioned substances are of different polarities, solvents of a certain polarity can only extract them to a different degree and thus produce a certain sensory profile.

solvents for extraction, have the following polarities: acetone (log P=−0.24), butan-1-ol (log P=0.88), butan-2-ol (log P=0.69), ethyl acetate (log P=0.71), ethanol (log P=−0.31), Ethyl methyl ketone (log P=0.37), methanol (log P=−0.77), methyl acetate (log=0.18), propan-1-ol (log=0.34) and propan-2-ol (log P=0.16).

Since numerous secondary components which are not sensorily active, such as polysaccharides, waxes, fats are also extracted during the extraction of fermented vanilla beans, the stabilisation of the vanilla extract plays an important role. Usually ethanol remains as solvent in the extract after extraction and thus stabilizes waxes, fats and other lipophilic substances which would precipitate without the use of a solubilizer.

Since, apart from ethanol, all common extraction solvents are limited in the end use either from toxicological (e.g. butan-1-ol, butan-2-ol, ethylmethylketone, methanol, methyl acetate, propan-1-ol and propan-2-ol) or sensory (e.g. acetone, ethyl acetate) aspects, the extraction solvent content must be reduced and an alternative stabilisation must be found. For example, the concentration of methanol in the final application must not exceed 1 mg/kg in the foodstuff. In addition, care must be taken to ensure that the extract is sufficiently concentrated to allow it to develop its flavour and remain microbiologically stable.

It is also known that a vanilla extract dissolved in ethanol changes its sensory profile during storage and, for example, in the language of the expert, develops fruity notes reminiscent of rum.

Previous approaches to solvent-free extraction of vanilla extracts are based on the use of water with additives.

In WO 2016 146837 A1, for example, a solid-liquid extraction of vegetable material with the use of non-ionic surfactants is described.

For example, WO 2006 047404 A2 reveals the fermentation of any plant starting material with a glucosidase, followed by aqueous extraction in the presence of another reactant, for example an amino acid or a sugar.

Both studies reveal neither a theory about the stabilization of the microbiologically unstable water extract nor a method for concentrating the extract.

EP 1 928 447 B1 describes a process in which crushed vanilla beans are extracted with an organic solvent such as ethanol and the extract is worked up by molecular distillation. However, no teaching is given on how the fractions of volatile and non-volatile flavourings obtained by distillation are combined to form an extract which is close to the starting material in terms of sensory properties.

However, there is an increasing societal demand for ethanol-free food.

It was therefore the task of the present invention to provide a process for obtaining an ethanol-free vanilla extract without the use of ethanol, which on the one hand has an authentic sensory profile which is close to that of the fermented vanilla beans used, and which is furthermore process and storage stable.

SUMMARY OF THE INVENTION

The present problem is solved by the subject-matter of the independent patent claims. Preferred formulations result from the wording of the dependent patent claims and the following description.

A first subject matter of the present invention relates to a process for the production of an ethanol-free vanilla extract, comprising the following steps:

(a) Preparation of fermented vanilla beans;
(b) Crushing/Cutting-up/Comminuting of the fermented vanilla beans;
(c) Extracting the crushed/cut-up/comminuted vanilla beans with an organic extraction solvent or an extraction solvent mixture comprising at least one organic extraction solvent having a log P value of from −0.8 to 0.4 to obtain a crude extract;
(d) Adding a protective solvent to the raw extract;
(e) Filtering of the raw extract;
(f) Distilling off the extraction solvent or the extraction solvent mixture from the crude extract to obtain a vanilla extract; and
(g) Optionally, phase separation and separation of the liquid vanilla extract freed from the extraction solvent or the extraction solvent mixture A further subject matter of the present invention relates to an ethanol-free vanilla extract, obtainable or obtained according to the above inventive step.

Furthermore, the present invention concerns an ethanol-free vanilla extract comprising a maximum of 100 mg/kg ethanol.

A further aspect of the present invention concerns the use of the ethanol-free vanilla extract for the production, in particular for the flavouring or reconstitution of the aroma, of foodstuffs, luxury foods, beverage products, semi-finished products, hygiene products, cosmetic or pharmaceutical products, tobacco products and products for animal nutrition.

Ultimately, the present invention relates to foodstuffs, luxury foods, beverage products, semi-finished products, hygiene products, cosmetic or pharmaceutical products, tobacco products as well as products for animal nutrition, which include the ethanol-free vanilla extract according to the invention.

DESCRIPTION OF THE FIGURES

FIG. 1 is a representation of sensory profiles of extracts of fermented vanilla beans produced by the method according to the invention.

FIG. 2 is a representation of the vanillin concentrations and soluble extract contents of acetone extracts and methanol extracts of fermented vanilla beans prepared by the method according to the invention. Vanillin contents (black bars, expressed as a percentage) and soluble extract contents (grey bars, expressed as a percentage) of acetone and methanol extracts of fermented vanilla beans according to the process according to the invention.

FIG. 3 is a representation of sensory profiles of extracts of fermented vanilla beans produced by the method of the invention as a function of the extraction temperature.

FIG. 4 shows the vanillin yields during a consecutive extraction with acetone and methanol. The solid line describes the vanillin contents of an extraction with acetone, the dashed line describes the vanillin contents of an extraction with methanol.

FIG. 5 is a representation of the vanillin yield during a consecutive extraction with methanol at different temperatures. The solid line describes the vanillin content of an extraction at 25° C., the dotted line describes the vanillin content of an extraction at 65° C.

DETAILED DESCRIPTION OF THE INVENTION

The term 'ethanol-free vanilla extract' means a vanilla extract which, with the exception of traces of ethanol naturally present in fermented vanilla beans, contains no ethanol and is produced without the use of ethanol.

In the process according to the invention for producing an ethanol-free vanilla extract, fermented vanilla beans are provided in a first step. The vanilla beans are fermented vanilla beans of the genus *Vanilla planifolia, Vanilla tahitensis* and *Vanilla pompona*.

The fermented vanilla beans are prepared as follows: Vanilla plants are grown in plantations. The vanilla pods are up to 30 cm long, botanically speaking they are capsule fruits, and are harvested shortly before they are ripe when they are yellow-green. At the time of harvesting, the green fruits do not yet have the typical aroma and taste of the finished product.

To obtain vanilla as a highly aromatic spice, the fruits must first undergo fermentation. For this purpose, it is first necessary to lyse the cells of the capsule fruits. This is done by conventional methods known from the state of the art, for example by physical processes such as treatment of the green vanilla pods with hot water or steam, freezing and thawing of the green vanilla pods, treatment of the green vanilla pods with $CO_2$ under pressure or enzymatic treatment of the green vanilla pods with cellulase, pectinases, etc. In this process step, on the one hand, glucovanillin, the precursor of vanillin, is released and, on the other hand, the β-glucosidases endogenously present in the green vanilla beans are released.

The vanilla beans are then fermented and dried, during which they lose water and take on their typical dark brown colour. During the drying and fermentation processes, hydrolysis transforms the glucovanillin into vanillin, the main aromatic substance of vanilla.

The fermented vanilla beans produced in this way usually have a moisture content of 10 to 30% and a vanillin content of 1 to 3% on dry matter.

The fermented vanilla beans described above are then, for use in the process according to the invention, crushed/cut-up/comminuted into small pieces of approximately 10 mm in size, for example cut, chaffed, cuttered, shredded, crushed or chopped, by conventional crushing methods that are known to experts in this field of technology, using granulators or shredders. The use of crushed vanilla beans facilitates subsequent extraction. It is clear that the smaller the ground vanilla beans or the larger the surface area of the crushed vanilla bean pieces, the easier the extraction of the vanilla beans is, taking into account, of course, the limitations associated with the industrial implementation of such a process. Preferably the size of the crushed vanilla bean particles is between 1 and 10 mm. If the degree of comminution is greater than that mentioned above, the ground vanilla bean becomes too pasty and complicates subsequent process steps such as filtration (clogging of the sieves) or distillation (boiling delay).

A pre-treatment of the vanilla bean pieces is not necessary in the process according to the invention.

After cutting-up/comminution, the vanilla bean pieces are extracted by maceration, digestion or percolation, whereby for the subsequent extraction the vanilla bean pieces are transferred, for example, to a Willmes press and circulation must be provided in order to increase the contact between the extraction material and the extraction solvent or extraction solvent mixture and thus the efficiency of the extraction.

In a further step of the process according to the invention, the flavourings of the crushed vanilla beans are extracted with an organic extraction solvent or an extraction solvent mixture comprising at least one organic extraction solvent with a log P value of −0.8 to 0.4 to obtain a crude extract.

To produce an ethanol-free vanilla extract according to the present invention, the use of ethanol having a log P value of −0.33 as an extraction solvent as such or in an extraction solvent mixture is excluded from the above definition.

Extraction is a physical process in which a starting material is exposed to a liquid, such as water, oil or a solvent, either on the whole or on the surface for some time, which serves as a solvent for certain ingredients and extracts the ingredients from the solid. The starting material as such is not dissolved, but only soluble components thereof are transferred into the solvent. The choice of solvent depends on its solubility with respect to the substance to be dissolved.

The log P value is defined as follows:

$$\log P = \log K(n\text{-octanol}/\text{water}) = \frac{C(n\text{-octanol})}{C(\text{water})},$$

wherein:
C (n-octanol) is the concentration of the solvent in the n-octanol phase; and
C (water) is the concentration of the solvent in the water phase K(n-octanol/water) is a dimensionless partition coefficient which indicates the ratio of the concentration of the solvent in a two-phase system of n-octanol and water. It is therefore a model measure for the polarity or water/fat solubility of the solvent.

The log P value is a common physical parameter and is positive for lipophilic solvents and negative for hydrophilic solvents.

Ultimately, the log P value of the extraction agent determines which flavouring substances are extracted qualitatively and quantitatively from the crushed vanilla bean particles.

It has been found that advantageous organic extraction solvents in the process according to the invention are: acetone (log=−0.24); methanol (log P=−0.77); propan-2-ol (log P=0.16); propan-1-ol (log P=0.34); methyl acetate (log P=0.18) and ethyl methyl ketone (log P=0.374).

An extraction solvent mixture according to the present invention comprises at least one of the above-mentioned organic extraction solvents in combination with another one of the group of the above-mentioned organic extraction solvents. In addition, an extraction-solvent mixture comprises at least one of the above-mentioned organic extraction solvents mixed with water. Furthermore, an extraction-solvent mixture according to the present invention comprises at least one of the above-mentioned organic extraction solvents in combination with a further organic solvent which is typically used as an ingredient of foodstuffs, for example vegetable oils, essential oils, sugar syrups, etc. Such vegetable oils are selected from the group consisting of sunflower, soybean, rape, peanut, palm, wheat germ, corn germ, olive and linseed oils.

When an extraction solvent mixture comprising at least one of the above-mentioned organic extraction solvents is used for extraction, the mixing ratio of organic extraction solvent to another organic solvent is in the range of 10:90 (v/v) to 90:10 (v/v), preferably in a ratio of 50:50 (v/v). When the extraction solvent is used in admixture with water, the mixing ratio of organic extraction solvent to water is in the range of 90:10 (v/v) to 60:40 (v/v), preferably in a ratio of 80:20 (v/v).

Preferably the above-mentioned extraction solvents are used pure.

Surprisingly, it was found that the extraction of the crushed/comminuted vanilla beans in step (c) of the process according to the invention with acetone, which has a log P-value −0.24, achieves particularly good results with respect to the sensory relevant ingredients, i.e. the value-giving aroma substances, compared to the other extraction solvents mentioned above.

In the extraction step according to the inventive method, the ratio of the amount of extraction solvent or extraction solvent mixture to the amount of vanilla beans used is important for an exhaustive extraction. With a high quantity of vanilla beans and a small quantity of extraction solvent or extraction solvent mixture, the extraction solvent or extraction solvent mixture quickly becomes saturated, so that the valuable ingredients cannot be completely extracted from the comminuted vanilla beans.

Conversely, too large a quantity of extraction solvent or extraction solvent mixture is not desirable, as the extract is then very diluted and its aroma no longer emerges. In addition, the evaporation of large quantities of extraction solvent or extraction solvent mixture is uneconomical from a procedural point of view. Large quantities of extraction solvents or extraction solvent mixture are also accompanied by longer evaporation times, which leads to more losses of valuable ingredients of the aroma extract and to the formation of dried fruit notes, of volatile carotenoid degradation products such as damascenones and of Strecker aldehydes, which in turn leads to the distribution of the aroma components in the vanilla extract and thus to a change of the sensory profile of the vanilla extract.

The extraction solvent or extraction solvent mixture is therefore used in excess of the amount of comminuted vanilla beans in the process according to the invention to ensure exhaustive extraction. Preferably, the extraction solvent or extraction solvent mixture is added to the quantity of comminuted vanilla beans in a range of 1:1 (w/w) to 40:1 (w/w). The most preferred ratio of extraction solvent or extraction solvent mixture to the amount of crushed/comminuted vanilla beans is 10:1 (w/w).

The extraction of the crushed/comminuted vanilla beans in the process according to the invention is to be carried out in a defined time/temperature profile. Surprisingly, it was found that an extraction at room temperature, for example, produces increasingly sweet, malty-smelling flavours. At an extraction temperature at higher temperatures of about 65° C., the solubility and thus the yield of the flavours to be extracted increases, while at the same time dried fruit notes are produced.

Preferably, the extraction of the crushed/comminuted fermented vanilla beans is carried out at a temperature range of 20 to 60° C. (preferably 30 to 60° C.) for a period of 8 to 20 hours. A longer extraction period involves the risk of degradation of valuable ingredients and the formation of dried fruit notes, volatile carotenoid degradation products such as damascenones and Strecker aldehydes, which in turn leads to the distribution of aroma components in the vanilla extract and thus influences the sensory profile of the vanilla extract. The extraction is most preferably carried out at a temperature of 40° C. for a total duration of 16 hours.

In the process according to the invention, the extraction of the crushed/comminuted vanilla beans is carried out in such a way that the extraction solvent or the extraction solvent mixture is consecutively renewed at least twice, but not more than five times. The extraction solvent or the extraction solvent mixture is preferably renewed consecutively at least three times. Consecutive extraction ensures an exhaustive extraction of the flavouring substances from the crushed/comminuted vanilla beans and thus maximizes the yield of flavouring substances.

After each extraction step, the raw extract obtained is decanted from the extraction material and the fractions of raw extract obtained from several consecutive extraction steps are combined into one raw extract.

The extraction solvent or extraction solvent mixture used in the process according to the invention must be completely removed from the raw extract either for sensory reasons, for example due to a strong inherent odour, or because of regulatory requirements. For example, acetone itself is an odorous substance with a threshold of 300 mg/kg which, with its fingernail varnish-like odour, adversely affects the sensory profile of the aroma extract produced with it. On the other hand, the European Union, for example, demands the removal of acetone up to the technically unavoidable level and the IOFI (International Organisation for the Flavour Industry) even demands a threshold of 2 mg/kg in the final application in its "Code of Practice". This is a set of rules that is applied internationally in the flavour industry.

In contrast, ethanol is an odorous substance with a threshold of 1,000 mg/kg, which is olfactorically unnoticeable even at a volume percentage in the final application, and which may be used in foodstuffs in unlimited quantities.

However, it is precisely when the extraction solvent or the extraction solvent mixture is removed by evaporation or distillation that losses of valuable components (e.g. by degradation) or the formation of interfering components (e.g. by oxidation) in the raw extract occur, thus leading to changes in the sensory profile of the vanilla extract obtained from it.

Surprisingly, it was found that losses of valuable components and the formation of interfering components can be avoided and particularly good sensory results can be achieved if a protective solvent is added to the raw extract before the extraction solvent or extraction solvent mixture is evaporated or distilled off. By using a protective solvent, the extraction solvent or the extraction solvent mixture can be gently removed from the raw extract without evaporating valuable aroma components or forming disturbing aroma components.

According to the invention, a protective solvent is understood to be a solvent which has a boiling point which is preferably at least 20° C. higher than the boiling point of the extraction solvent used in step (c) of the process according to the invention or of the at least one organic extraction solvent in the extraction solvent mixture used.

In particular, the protective solvent is a solvent selected from the group consisting of 1,2-propanediol, 1,3-propanediol, diacetin (glyceryl diacetate), triacetin, triethyl citrate and solubilizing foods such as vegetable oils.

Since the expert in the present field of technology is very familiar with the chemical and physical properties of the extraction solvents or extraction-solvent mixtures, especially their boiling points, he knows which protective solvent to choose from the above-mentioned group, depending on the extraction solvent or extraction-solvent mixture used, in order to comply with the above condition.

Since the extraction solvent or extraction solvent mixture used in step (c) of the process according to the invention for extracting the crushed/comminuted vanilla beans and the protective solvent have significantly different boiling points, no azeotrope is formed during evaporation or distillation, and the extraction solvent or extraction solvent mixture can be cleanly and completely removed from the crude extract.

Surprisingly, it was found that the use of 1,2-propanediol particularly facilitates the evaporation or distillation of the extraction solvent or the extraction solvent mixture from the raw extract with a residual amount of less than 1,000 mg/kg at a vacuum below 10 mbar without significantly losing valuable aroma components of the raw extract.

1,2-propanediol, also known as propylene glycol, is a clear, colourless, almost odourless liquid with a boiling point of 188.2° C. 1,2-Propanediol belongs to the polyvalent alkanols and is chiral at C2, so there is an (R)-enantiomer and an (S)-enantiomer. 1,2-Propanediol is approved in the EU as a food additive. In the preparation of food flavourings 1,2-propanediol is used as carrier. 1,2-Propanediol can be used as a racemate, as an R or S enantiomer or as any mixture of its enantiomers.

For the complete removal of the extraction solvent or the extraction solvent mixture on the one hand and for obtaining an authentic vanilla extract on the other hand, the ratio of the amount of vanilla beans used to the amount of protective solvent is decisive. With a large amount of vanilla beans and a small amount of protective solvent a very concentrated vanilla extract is obtained. However, a saturation of the protective solvent phase with value-adding aroma substances occurs more quickly, with the consequence that value-adding components are already lost during the evaporation of the extraction solvent or the extraction solvent mixture. On the other hand, too high a quantity of protective solvent is not desirable, since the extract is then very diluted and only smells weakly.

Preferably, the ratio of the amount of vanilla beans used to the amount of protective solvent added to the raw extract is in the range of 1:10 (w/w) to 10:1 (w/w). A ratio of the amount of vanilla beans used to the amount of protective solvent added in a range of 1:1 (w/w) to 4:1 (w/w) before removing the extraction solvent or the extraction solvent mixture from the raw extract has proved to be particularly advantageous.

Before removing the extraction solvent or the extraction solvent mixture, the raw extract mixed with the protective solvent is filtered. Alternatively, the raw extract can be filtered before the protective solvent is added. The filtration is carried out by means of suitable commercial filters, preferably plate filters with 2.9 mm thick cellulose plates with a water permeability of 10200 l/m$^2$/min and exclusion of 700 g/m$^2$, in order to remove solid, non-dissolvable components from the vanilla extraction.

The filtered raw extract thus obtained is then placed in a suitable distillation still.

In a further step of the process according to the invention, the extraction solvent or the extraction solvent mixture is removed from the raw extract by distillation.

Evaporation or distillation of the extraction solvent or the extraction solvent mixture from the raw extract is initially carried out gently and close to the boiling point of the extraction solvent or the extraction solvent mixture. Evaporation or distillation is preferably carried out at a temperature in the range of 20 to 60° C. and a vacuum of 1 to 500 mbar (preferably 10 to 500 mbar). Evaporation of the extraction solvent or extraction solvent mixture at a temperature of 40° C. and/or a vacuum of 100 mbar has proven to be particularly advantageous. In this process, the raw extract is first freed from >99% of the extraction solvent or the extraction solvent mixture.

In order to keep the contact time between the material to be distilled, i.e. in this case the raw extract, and the evaporator as short as possible, the distillation in the process according to the invention is preferably carried out in a falling film evaporator, rotary evaporator or thin film evaporator or by means of a spinning cone process.

In the above-mentioned evaporators, solutions or solvent mixtures are evaporated in a thin film. Due to a high heat transfer coefficient, a fast and efficient evaporation of the extraction solvent or extraction solvent mixture takes place. Since the devices can be operated very well in vacuum, they are suitable for the gentle distillation of solvent mixtures at low temperatures.

Alternatively, the extraction solvent or extraction solvent mixture is removed in a spinning cone process. This is a rectification column with rotating conical inserts. Ribs are attached to the underside of the cones which create turbulence in the gas phase and thus ensure an intensive mass transfer between liquid and vapor. Since the working temperatures are very mild, heat damage to the distillation product is avoided.

All of the above-mentioned evaporation processes enable a very gentle removal of the extraction solvent or the extraction solvent mixture without significant losses of valuable aroma components in the raw extract.

When evaporating or distilling off the extraction solvent or extraction-solvent mixture, it is important that, for sensory reasons, for example due to a strong inherent odour, as well as regulatory requirements, the last remaining amounts of extraction solvent and/or water, which either originate naturally from the crushed/comminuted fermented vanilla beans or from the extraction-solvent mixture, are removed from the raw extract. The removal of residual water is particularly important to ensure that the extract is microbiologically stable and thus durable.

After removal of >99% of the extraction solvent or the extraction solvent mixture from the raw extract, the vacuum is reduced to 20 mbar during distillation in order to remove even the last residual amounts of extraction solvent and/or water to less than 1,000 mg/kg from the vanilla extract thus obtained.

After distilling off the extraction solvent or the extraction solvent mixture ≥90%) of the protective solvent used, in particular 100% of the protective solvent used, based on the originally added amount of 1,2-propanediol, remain in the vanilla extract obtained.

During the extraction of the comminuted vanilla beans in step (c) of the process according to the invention, numerous secondary components which are not sensorily active, such as waxes and fats, are also extracted in addition to the value-giving aroma substances, depending on the polarity of the extraction solvent or the extraction solvent mixture used. Therefore, the stabilization of the vanilla extract plays an important role.

In the case of vanilla extracts produced using the state of the art technology using ethanol, ethanol remains as a solvent in the vanilla extract after extraction and stabilises waxes and other lipophilic substances which would cause solubility problems and precipitate without the use of a solubiliser.

In a further optional step of the process according to the invention, the vanilla extract is freed from the lipophilic waxy phase. To separate the lipophilic waxy phase, the vanilla extract freed from the extraction solvent or extraction solvent mixture is simply left to stand at a temperature in the range of 10 to 40° C., or 20 to 40° C., preferably at a temperature of 30° C. During a settling period of 10 to 48 hours, a phase separation into a wax phase and a liquid vanilla extract phase takes place in the vanilla extract. During this time, the transition of value-giving aromatic substances into the wax phase is limited and the time of phase separation is optimal, as can be seen from Table 1 below.

After phase separation, the wax phase is separated from the liquid vanilla extract phase by draining the liquid vanilla extract phase from the distillation bubble. The wax phase is discarded.

TABLE 1

Selected phenols and fatty acids in the wax phase and the dewaxed acetone vanilla extract according to example 1 (SBSE-GCMS)

| Connection | Dewaxed vanilla extract [mg/kg] | Wax phase [mg/kg] |
| --- | --- | --- |
| vanillin | 76.735 | 0.628 |
| guaiacol | 16.100 | 0.000 |
| 4-methylguaiacol | 9.828 | 0.000 |
| methyl cinnamate | 7.876 | 0.000 |
| p-hydroxybenzaldehyde | 5.999 | 0.000 |
| palmitic acid | 4.608 | 141.915 |
| lauric acid | 2.248 | 29.083 |
| ethyl cinnamate | 2.188 | 0.000 |
| capric acid | 1.753 | 0.000 |
| myristic acid | 1.009 | 39.572 |

The analysis results in Table 1 show that only traces of value-giving phenols are detectable in the wax phase. The wax phase is characterized by fatty acids and their glycerides and fatty alcohol esters.

The results shown in Table 1 were obtained using SBSE-GCMS from the acetone extract prepared according to Example 1 described below. SBSE (Stir Bar Sorptive Extraction) is a method of sample preparation for subsequent analysis by gas chromatography. The method is based on the use of a sorbent coated magnetic stirring rod which mixes the sample to be analysed (dewaxed vanilla extract or wax phase), whereby the analytes accumulate in the coating material.

Since 1,2-propanediol has an antimicrobial effect in a concentration of >1%, the addition of 1,2-propanediol to the crude extract before the extraction solvent or extraction solvent mixture in the above-mentioned ratio evaporates has the additional advantage that the extract is stabilized after the extraction solvent has been removed. Thus, the vanilla extract is both microbiologically stable and protected against oxidation.

Surprisingly, the storage of the vanilla extract in 1,2-propanediol does not lead to a change in the odour type, whereas storage in ethanol, for example, produces fruity notes reminiscent of rum.

The vanilla beans extracted with acetone, ethanol, methanol, 2-propanol, ethyl acetate and a mixture of 65% methanol/35% water yielded extracts with the sensory profiles shown in FIG. 1.

The extracts were prepared as follows: 37.5 g of crushed vanilla beans were extracted into a 300 ml Erlenmeyer flask with magnetic stirrer with 150 g acetone or 150 g ethanol or 150 g methanol or 150 g 2-propanol or 150 ethyl acetate or a mixture of 65% methanol/35% water as extraction solvent for 2 h. Before distillation, 50 g diacetin was added to the respective raw extracts. The extraction solvent was removed from the raw extract samples obtained on a rotary evaporator at a temperature of 50° C. and a vacuum of 250 to 40 mbar. The obtained vanilla extracts were sensory evaluated in milk as matrix in a concentration of 0.1 to 0.3%.

To create a sensory profile, the descriptive terms (descriptors) are first collected in the panel, whereby the lists of terms are structured, similar terms are combined and hedonic attributes are eliminated. The assessment of the intensity of the descriptors on a scale of 1 to 10 is carried out by at least ten trained test persons. The samples are coded, tasted in a sensory room in a randomised sequence and excluding disturbing influences such as colour, noise and foreign odours. The final result is determined by summing the individual results and then forming the arithmetic mean and is presented graphically in the form of a network diagram.

The sensory evaluation of the extracts obtained showed that phenolic, balsamic notes are particularly pronounced in the acetone-vanilla extract. Surprisingly, the aroma profile of the acetone vanilla extract was described by the panelists as significantly more authentic, i.e. closer to the aroma profile of the fermented vanilla beans used, than a vanilla extract obtained using ethanol.

A comparison of the proportion of extracted substances and the concentration of vanillin also showed that acetone extracts the value-giving aroma substance vanillin more selectively than, for example, methanol, as can be seen in FIG. 2. The concentration of the extract after evaporation of the extraction solvent corresponds to the proportion of dry matter soluble in the extraction solvent. Acetone extracts half of the minor components and twice the amount of vanillin in one extraction step compared with methanol. Thus, acetone seems to extract sensory relevant components preferentially compared to the other solvents.

Other valuable flavouring substances extracted during extraction with acetone are in particular the compounds listed below. The term "value-adding flavouring substances" means those flavouring substances which contribute significantly to an authentic sensory profile of an extract.

The value-giving aroma substances of an acetone-vanilla extract include phenols: in particular guaiacol, 4-methylguajacol, p-cresol, 4-vinylguajacol, 2-vinylphenol, acetovanillone, vanillyl alcohol, p-hydroxybenzaldehyde and p-hydroxybenzyl alcohol, and esters: in particular methyl salicylate, methyl cinnamate and ethyllinolenate.

The extracts were prepared as follows:

Acetone extract and methanol extract: extraction temperature: 60° C.; pressure: 5 bar: In a 2,000 ml pressure vessel (autoclave station F. Struever), 400 g of crushed/comminuted vanilla beans were placed in each case and 800 g of acetone or methanol were added as extraction solvent. A pressure of 2 bar was then applied. After heating up to 60° C., the pressure was set to 5 bar and extraction was continued for 2 h. After cooling, the mixture was passed through a kitchen sieve and filtered. The crushed vanilla beans were then extracted twice consecutively with 800 g acetone or methanol under the same conditions. Before the respective raw extracts were combined, a sample was taken from each phase for analysis. The combined raw extracts were concentrated on the rotary evaporator under a vacuum of 40 mbar, a temperature of 45° C. and 30 min at ultimate vacuum.

|  | Extraction | Acetone extract | Methanol extract |
| --- | --- | --- | --- |
| Vanillin content(mg/kg) in the liquid phase | 1st stage | 8,402 | 7,115 |
|  | 2nd stage | 2,582 | 2,425 |
|  | 3rd stage | 851 | 775 |
| Weighing out combined raw extracts (g/400 g vanilla beans) |  | 59.9 | 116.6 |
| Vanillin content Extract solvent-free (%) |  | 9.7 | 4.9 |

Acetone extract and methanol extract: extraction temperature: 40° C.; pressure: atmospheric pressure: 400 g each of shredded vanilla beans were placed in a 4000 ml three-necked flask and 1000 g each of acetone or methanol were added as extraction solvent. After heating to 40° C., extraction was carried out for 2 h. After cooling, the mixture was passed over a kitchen sieve and filtered. The crushed vanilla was then extracted twice consecutively with 1,000 g of acetone or methanol each under the same conditions. Before the respective raw extracts were combined, a sample was taken from each phase for analysis. The combined raw extracts were concentrated on the rotary evaporator under a vacuum of 40 mbar, a temperature of 45° C. and 30 min at ultimate vacuum.

|  | Extraction | Acetone extract | Methanol extract |
| --- | --- | --- | --- |
| Vanillin content (mg/kg) in the liquid phase | 1st stage | 5,208 | 5,353 |
|  | 2nd stage | 1,399 | 1,620 |
|  | 3rd stage | 386 | 545 |
| Weighing out combined raw extracts (g/400 g vanilla beans) |  | 48.3 | 132.4 |
| Vanillin content Extract solvent-free (%) |  | 9.0 | 4.7 |

The influence of temperature on the sensory profile using the example of an extraction of crushed fermented vanilla beans with methanol is shown in FIG. 3. As can be seen from FIG. 3, the sensory profile of the vanilla extract, where the extraction was carried out three times with methanol for 2 hours each at a temperature of 40° C., is characterised by phenolic notes, whereas in the vanilla extracts obtained at a temperature of 30° C. and 60° C., sweet flavours and dried fruit notes dominate the sensory profile.

The extracts were prepared as follows: 37.5 g of crushed vanilla beans each containing 150 g of methanol as extraction solvent at a temperature of 30° C., 40° C. or 65° C. or 150 g of methanol/water as extraction solvent at a temperature of 65° C. were extracted into a 300 ml Erlenmeyer flask with magnetic stirrer for 2 h. The crushed/comminuted vanilla beans were then extracted twice consecutively with 150 g methanol or 150 g methanol/water methanol under the same conditions. The combined raw extracts were filtered off. Before distillation, 50 g diacetin was added to the respective raw extracts. The extraction solvent was removed from the raw extract samples obtained on a rotary evaporator at a temperature of 50° C. and a vacuum of 50 mbar. The obtained vanilla extracts were sensory evaluated in milk as matrix in a concentration of 0.1 to 0.3%.

The influence of consecutive extraction with acetone or methanol on the vanillin yield is shown in FIG. 4. As can be seen in FIG. 4, significant vanillin yields are still obtained in extraction stages 2 and 3: the solid line describes the vanillin content of an extraction with acetone: 5,208 mg/kg (extraction 1) plus 1,399 mg/kg (extraction 2) plus 386 mg/kg (extraction 3); the dotted line describes the vanillin contents of an extraction with methanol: 5,353 mg/kg (extraction 1) plus 1,620 mg/kg (extraction 2) plus 545 mg/kg (extraction 3). In addition, for an exhaustive extraction at a temperature of 40° C., the yield of dry matter soluble in acetone or methanol is about 10 to 40%.

Acetone extract and methanol extract: extraction temperature: 40° C.; pressure: atmospheric pressure: 400 g each of shredded vanilla beans were placed in a 4,000 ml three-necked flask and 1,000 g each of acetone or methanol were added as extraction solvent. After heating to 40° C., extraction was carried out for 2 h. After cooling, the mixture was passed over a kitchen sieve and filtered. The crushed vanilla was then extracted twice consecutively with 1,000 g of acetone or methanol each under the same conditions. Before the respective raw extracts were combined, a sample was taken from each phase for analysis. The combined raw extracts were concentrated on the rotary evaporator under a vacuum of 40 mbar, a temperature of 45° C. and 30 min at ultimate vacuum.

|  | Extraction | Acetone extract | Methanol extract |
|---|---|---|---|
| Vanillin content (mg/kg) in the liquid phase | 1st stage | 5,208 | 5,353 |
|  | 2nd stage | 1,399 | 1,620 |
|  | 3rd stage | 386 | 545 |
| Weighing out combined raw extracts (g/400 g vanilla beans) |  | 48.3 | 132.4 |
| Soluble dry matter (%) |  | 12 | 33 |

The influence of consecutive extraction with methanol on vanillin yield at different temperatures is shown in FIG. 5. As can be seen in FIG. 5, extraction at 65° C. leads to a better vanillin yield than extraction at 25° C. because of the higher solubility of the aromatic substances of the vanilla beans in the extraction solvent: the solid line describes the vanillin content of an extraction with methanol at 65° C.: 7,251 mg/kg (extraction 1) plus 2,031 mg/kg (extraction 2) plus 616 mg/kg (extraction 3); the dotted line describes the vanillin content of an extraction with methanol at 25° C.: 6195 mg/kg (extraction 1) plus 1446 mg/kg (extraction 2) plus 305 mg/kg (extraction 3). On the other hand, the higher solubility and thus the yield of flavouring substances is limited by the sensory properties (see above).

The extracts were prepared as follows: 37.5 g of crushed vanilla beans were extracted in a 300 ml Erlenmeyer flask with magnetic stirrer, each containing 150 g of methanol as extraction solvent, at a temperature of 25° C. or 65° C. for 2 h. The comminuted/crushed vanilla beans were then extracted twice consecutively with 150 g methanol each under the same conditions. The combined raw extracts were filtered off. Before distillation, 50 g diacetin was added to the respective raw extracts. The extraction solvent was removed from the obtained raw extract samples on a rotary evaporator at a temperature of 50° C. and a vacuum of 50 mbar.

|  | Extraction | Methanol extract 65° C. | Methanol extract 25° C. |
|---|---|---|---|
| Vanillin content (mg/kg) in the liquid phase | 1st stage | 7,251 | 6,195 |
|  | 2nd stage | 2,031 | 1,446 |
|  | 3rd stage | 616 | 305 |

The present invention further relates to an ethanol-free vanilla extract obtainable by the process described above.

The vanilla extract produced by the process according to the invention is characterized by the fact that it contains only residual amounts of ethanol that occurs naturally in fermented vanilla beans or is produced during the ripening or fermentation of the vanilla beans, so that it can be sold to countries where the consumption of alcohol is prohibited for cultural, religious or ideological reasons.

In addition, the vanilla extract produced by the process according to the invention is characterized in that it has an authentic sensory profile with phenolic, balsamic notes which is closer to the sensory profile of fermented vanilla beans than a vanilla extract obtained by the same process using ethanol.

The vanilla extract produced according to the invention is microbiologically stable and does not lead to a change in the odour type during storage.

Components of an ethanol-vanilla extract and an acetone-vanilla extract prepared by the same extraction method and from the same fermented vanilla beans are listed in Table 2 below.

The acetone vanilla extract was prepared as described in example 1 below. The ethanol-vanilla extract was prepared by the same extraction procedure and from the same batch of fermented vanilla beans as described in example 1 below, except that ethanol was used as the extraction solvent instead of acetone.

The results shown in Table 2 were obtained as follows: 100 mg of extract is placed in a 10 ml glass vessel and diluted with 4 g of water with the addition of the internal standard 2-nonanol (20 mg/kg). A PDMS-coated magnetic stirring rod (10 mm long, 1 mm path length) is added and stirred for 1 h. The magnetic stirring rod is then removed, another magnetic stirring rod is used for extraction in the same way and both magnetic stirring rods are then heated at 150° C. using a thermodesorption unit on the GC. The volatile compounds are applied to the chromatographic system (capillary column with WAX coating 30 m×0.25 mm×0.25 µm), separated (temperature program from 40° C. with 3° C./min to 230° C.) and analysed by mass spectrometry. The peak areas are then placed in the ratio to 2-nonanol and output as content data, taking response factors into account.

The content of the individual compounds of the ethanol and acetone vanilla extracts is given as a percentage by area in relation to the peak area of the 2-nonanol used.

TABLE 2

Comparison of composition of an ethanol-vanilla extract and an acetone-vanilla extract

| Connection | Ethanol vanilla extract Percentage by area | Acetone vanilla extract Percentage by area |
|---|---|---|
| vanillin | 54.848 | 52.296 |
| 3-methylbutanal-propylenglycolacetal isomer 1 | n.a. | 0.062 |
| guaiacol | 3.839 | 10.972 |
| p-hydroxybenzaldehyde | 0.940 | 4.088 |
| capric acid | 0.372 | 1.194 |
| methyl cinnamate | 12.708 | 5.367 |
| 3-methylbutanal-propylenglycolacetal isomer 2 | n.n. | 0.055 |
| 4-methylguaiacol | 3.357 | 6.698 |
| nonanal | 0.502 | 0.246 |
| 4-vinylguaiacol | 0.360 | 0.207 |
| hexanol | 0.221 | 0.233 |
| methylanisate | 0.480 | 0.300 |
| isoamyl acetate | 0.078 | n.a. |
| γ-nonalactone | 0.288 | 0.377 |
| decanal | 0.094 | 0.038 |
| anisaldehyde | 0.141 | 0.791 |
| p-cresol | 0.081 | 0.222 |
| 2E,4E-nonadienal | n.n. | 0.162 |
| pentanal diethyl acetal | 0.066 | n.a. |
| phenylacetaldehyde diethylacetal | 0.158 | n.a. |
| acetaldehyde diethyl acetal | 1.399 | n.a. |
| 2-methylpropanal diethyl acetal | 0.215 | n.a. |
| 2-methylbutanal diethyl acetal | 0.356 | n.a. |
| hexanal diethyl acetal | 0.457 | n.a. |
| 2-pentylfuran | 0.030 | 0.012 |

TABLE 2-continued

Comparison of composition of an ethanol-vanilla extract and an acetone-vanilla extract

| Connection | Ethanol vanilla extract Percentage by area | Acetone vanilla extract Percentage by area |
|---|---|---|
| γ-non-2-enolactone | n.n. | 0.167 |
| γ-octalactone | n.n. | 0.040 |
| γ-decalactone | 0.057 | 0.121 |
| vanillinethylether | 10.627 | 1.060 |
| cinnamaldehyde | 0.052 | 0.019 |
| 3-phenylpropyl alcohol | 0.032 | 0.029 |
| anisylethylether | 0.280 | n.n. |

Note:
n.n. = not detected

In contact with vanilla ingredients, ethanol forms rum-like flavours, which can be recognised by the formation of ethers, esters and acetals, among other things, as shown in Table 2. Such compounds are not present at all or only in small amounts in the acetone vanilla extract.

On the other hand, acetone does not form detectable reaction products when in contact with vanilla ingredients The acetone-based vanilla extract has phenolic, balsamic notes, which can be recognized by the presence of guaiacol, 4-methylguaiacol, p-cresol, 4-vinylguaiacol, 2-vinylphenol, acetovanillone, vanillyl alcohol, p-hydroxybenzaldehyde and p-hydroxybenzyl alcohol, among others.

The present invention thus also concerns an ethanol-free vanilla extract with an ethanol content of not more than 100 mg/kg, in particular not more than 50 mg/kg. The ethanol content is derived from ethanol naturally present in the vanilla beans or produced during the ripening of the vanilla beans, for example as a degradation product of mono-, di- or polysaccharides naturally present in vanilla beans. The vanilla extract is therefore preferably free of externally added ethanol or non-natural ethanol. In particular, the vanilla extract is free of ethanolic extraction solvents.

In a preferred embodiment, the present invention relates to an ethanol-free vanilla extract having a lower content of ether compounds compared to an ethanol-vanilla extract of the same concentration produced by the same extraction process and from the same dried vanilla beans. As can be seen from Table 2 above, the composition of the acetone-based vanilla extract has a vanillin ethyl ether content (expressed as a percentage by area) which is at least 70%, preferably at least 80%, lower than the vanillin ethyl ether content (expressed as a percentage by area) of an ethanol-vanilla extract of the same concentration prepared by the same extraction method and from the same fermented vanilla beans.

In a further preferred embodiment, the present invention relates to an ethanol-free vanilla extract, the composition of which comprises guaiacol in an amount (expressed as a percentage by area) which is at least 200% greater than the amount of guaiacol (expressed as a percentage by area) in an ethanol-vanilla extract of the same concentration prepared by the same extraction process and from the same fermented vanilla beans.

In addition, the ethanol-free vanilla extract of the invention is characterized in that it comprises p-hydroxybenzaldehyde in an amount (expressed as area percent) at least 300% greater than the amount of p-hydroxybenzaldehyde (expressed as area percent) in an ethanol-vanilla extract of the same concentration prepared by the same extraction method and from the same fermented vanilla beans.

In another likewise preferred embodiment, the present invention relates to an ethanol-free vanilla extract in which the quantitative ratio of the guaiacol contained in the vanilla extract to the vanillin contained in the vanilla extract (determined on the basis of the peak areas determined by the preceding chromatographic method—GCMS, set in relation to the internal standard 2-nonanol) lies in a range from 1 to 0.001. In this context, a ratio of guaiacol to vanillin in the range from 0.40 to 0.05 is particularly preferred; a ratio in the range from 0.35 to 0.10 is extremely preferred.

In addition, it is preferred that the ethanol-free vanilla extract, obtained according to the methodology of the invention, has a high ratio of p-hydroxybenzaldehyde to the vanillin contained in the extract. A quantitative ratio of p-hydroxybenzaldehyde to vanillin in the range from 0.001 to 0.1 is particularly preferred; a quantitative ratio in the range from 0.02 to 0.08 is extremely preferred.

Furthermore, it is preferred that the ethanol-free vanilla extract obtained according to the methodology of the invention has a low quantity ratio of acetals, such as 3-methylbutanal-propylene glycol acetal isomer 1 or 3-methylbutanal-propylene glycol acetal isomer 2, and ethers, such as anisylethylether or vanillin ethyl ether, in relation to the vanillin contained in the ethanol-free vanilla extract.

A particularly preferred embodiment of the present invention concerns an ethanol-free vanilla extract with a quantitative ratio of acetal compounds, such as 3-methylbutanal-propylene glycol acetal isomer 1 or 3-methylbutanal-propylene glycol acetal isomer 2, to vanillin in a range of 0.0005 to 0.01. Most preferred is a quantitative ratio of said acetal compounds to vanillin in a range of 0.0009 to 0.005.

In addition, it is particularly preferred that the ratio of the ether compounds contained in the ethanol-free vanilla extract, such as anisylethylether or vanillinethylether, to the vanillin contained in the extract is in the range of 0.001 to 0.1. Most preferred is a ratio of said ether compounds to vanillin in a range of 0.01 to 0.4.

What is surprising here is that vanilla extracts (produced according to the process according to the invention) with a content of guaiacol, p-hydroxybenzaldehyde, ethers and acetals in the areas described above are characterized by the fact that they have a particularly authentic sensory profile with phenolic, balsamic notes, which is closer to the sensory profile of fermented vanilla beans than comparable vanilla extracts with different ratios of guaiacol, ethers and acetals.

Since after the extraction solvent or the extraction solvent mixture has evaporated, the wax phase is separated from the liquid vanilla extract phase, the ethanol-free vanilla extract according to the present invention is also characterized in that it is free of waxes and fats, in particular fatty acids, their glycerides and fatty carbon esters, which would otherwise cause solubility problems and precipitate.

The ethanol-free vanilla extract according to the invention can be used for the production of foodstuffs, luxury foods, beverage products, semi-finished products, hygiene products, cosmetic or pharmaceutical products, tobacco products and products for animal feed. In particular, the vanilla extract according to the invention can be used for flavouring or reconstituting the aroma of foodstuffs, luxury foods, beverage products, semi-finished products, hygiene products, cosmetic or pharmaceutical products, tobacco products as well as products for animal nutrition.

A further aspect of the present invention is therefore also food, semi-luxury food, beverage products, semi-finished products, hygiene products, cosmetic or pharmaceutical products, tobacco products as well as products for animal nutrition which include the ethanol-free vanilla extract. The foods to which the vanilla extract according to the invention is added are preferably selected from the group consisting of beverages, dairy products, sweets, food supplements, dietary foods and food surrogates without being limited thereto.

EXAMPLE

The process according to the present invention and the ethanol-free vanilla extract obtained thereby is now described in more detail by means of the following example.

Example 1: Preparation of an Acetone-Vanilla Extract 25 kg of sliced fermented vanilla beans (*Vanilla planifolia*) are placed in a Willmes press and the first portion of 60 kg of acetone is added at 40° C. The pods are extracted at 40° C. for 4 hours with the drum rotating, then cooled to 30° C. and the raw acetone extract is drained through a 200 µm filter bag. The pods are extracted a total of four times with the corresponding subset of 60 kg of acetone in a manner comparable to that used for the extraction. The combined acetone raw extracts are mixed with 7.5 kg 1,2-propanediol and homogenized under stirring. The mixture is filtered through a plate filter with 2.9 mm thick cellulose plates with a water permeability of 10200 L/m²/min and exclusion of 700 g/m² and placed in a suitable distillation bubble. At 50° C. and a vacuum of 500 to 600 mbar the raw extract is first freed from >99% of the acetone. The vacuum is then reduced to 20 mbar to remove even the water and the last remaining acetone to less than 1,000 mg/kg. The vanilla extract freed from acetone is left standing. Within 24 hours at a temperature of 3° C. the vanilla extract separates into a lower liquid polypropylene glycol phase and an upper wax phase. The liquid polypropylene glycol phase (7.5 kg) is separated from the wax phase and the wax phase is discarded.

The acetone-based vanilla extract prepared by the method described above was analysed by gas chromatography as follows: 100 mg of extract was placed in a 10 ml glass vessel and diluted with 4 g of water with the addition of the internal standard 2-nonanol (20 mg/kg). A magnetic stirring rod coated with PDMS (10 mm long, 1 mm path length) is added and stirred for 1 h. The magnetic stirring rod is then removed, another magnetic stirring rod is used for extraction in the same way and both magnetic stirring rods are then heated at 150° C. using a thermodesorption unit on the GC. The volatile compounds are transferred to the chromatographic system (capillary column with WAX coating 30 m×0.25 mm×0.25 µm), separated (temperature program from 40° C. with 3° C./min to 230° C.) and analysed by mass spectrometry. The peak areas are then placed in the ratio to 2-nonanol and output as content data, taking response factors into account.

The composition of the acetone-based vanilla extract is shown in Table 3.

TABLE 3

Composition of volatile components of an acetone-based vanilla extract according to the invention

| Connection | Concentration [mg/kg] |
|---|---|
| vanillin | 76.735 |
| propanone-1,2-propylene glycol ketal | 27.372 |
| guaiacol | 16.100 |
| 4-methylguaiacol | 9.828 |

TABLE 3-continued

Composition of volatile components of an acetone-based vanilla extract according to the invention

| Connection | Concentration [mg/kg] |
|---|---|
| E-methylcinnamate | 7.876 |
| p-hydroxybenzaldehyde | 5.999 |
| benzoic acid | 5.488 |
| palmitic acid | 4.608 |
| lauric acid | 2.248 |
| E-ethylcinnamate | 2.188 |
| capric acid | 1.753 |
| hexanal-1,2-propylene glycol acetal isomer | 1.611 |
| 2 E-decenal | 1.528 |
| anisaldehyde | 1.161 |
| phenol | 1.093 |
| myristic acid | 1.009 |
| 2 E-octenol | 0.878 |
| 2 E-heptenal | 0.855 |
| methyl salicylate | 0.754 |
| octanol | 0.592 |
| 2 E,4 E-decadienal | 0.577 |
| anisyl alcohol | 0.572 |
| γ-nonalactone | 0.554 |
| eugenol | 0.506 |
| 2 E-nonenal | 0.496 |
| 1,3-octenol | 0.493 |
| methylanisate | 0.440 |
| methyl vanillate | 0.440 |
| anisyl acetate | 0.422 |
| heptanoic acid | 0.410 |
| trans-anethole | 0.364 |
| nonanal | 0.362 |
| caproic acid | 0.354 |
| Z-methyl cinnamate | 0.349 |
| hexanal | 0.341 |
| p-cresol | 0.326 |
| octanal | 0.321 |
| 4-vinylguaiacol | 0.303 |
| hexanal-1,2-propylene glycol acetal isomer | 0.286 |
| acetophenone | 0.278 |
| 2-hydroxy-2-cyclopentenone | 0.266 |
| phenylacetaldehyde-1,2-propylene glycol acetal isomer | 0.205 |
| 4-ethylguaiacol | 0.195 |
| furfural | 0.192 |
| γ-decalactone | 0.177 |
| diacetone alcohol | 0.147 |
| 2 E-octenal | 0.147 |
| 2-phenylethyl alcohol | 0.134 |
| ethyldihydrocinnamate | 0.111 |
| 4-hydroxybenzyl methyl ether | 0.101 |
| anisylformate | 0.099 |
| 3-hydroxy-4-methoxybenzyl alcohol | 0.099 |
| salicylaldehyde | 0.096 |
| 3-methylbutanal-propylenglycolacetal isomer-1 | 0.091 |
| 3-methylbutanal-propylenglycolacetal isomer-2 | 0.081 |
| heptanal 1,2-propylene glycol acetal isomer | 0.073 |
| octanal 1,2-propylene glycol acetal isomer | 0.073 |
| α-ionone | 0.068 |
| Z-ethylcinnamate | 0.068 |
| methyl caprylate | 0.058 |
| γ-octalactone | 0.058 |
| couminaldehyde | 0.046 |
| benzaldehyde propylene glycol acetal isomer | 0.046 |

The invention claimed is:

1. An ethanol-free vanilla extract obtainable by a process comprising:
(a) preparing fermented vanilla beans;
(b) crushing the fermented vanilla beans;
(c) extracting the crushed vanilla beans with an organic extraction solvent or an extraction solvent mixture comprising at least one organic extraction solvent having a log P value of from −0.8 to 0.4 to obtain a raw extract, wherein the organic extraction solvent having a log P value of −0.8 to 0.4 is selected from the group consisting of methanol, acetone, propan-2-ol, propan-1-ol, methyl acetate, ethyl methyl ketone, and a combination of any of the foregoing;
- (d) adding a protective solvent to the raw extract, wherein the protective solvent is selected from the group consisting of 1,2-propanediol, 1,3-propanediol, diacetin (glyceryl diacetate), triacetin, and triethyl citrate;
- (e) filtering the raw extract; and
- (f) distilling off the extraction solvent or the extraction solvent mixture from the raw extract to obtain a vanilla extract.

2. The extract of claim 1 wherein the process further comprises phase separating and separating the liquid vanilla extract freed from the organic extraction solvent or extraction solvent mixture.

3. The extract of claim 1, having an ethanol content not exceeding 100 mg/kg.

4. The extract of claim 3, having an ethanol content not exceeding 50 mg/kg.

5. The extract according to claim 1, wherein extracting the crushed vanilla beans is carried out with acetone.

6. The extract according to claim 1, wherein the extraction solvent or the extraction solvent mixture is added to the crushed vanilla beans in a ratio in a range of 1:1 (w/w) to 40:1 (w/w).

7. The extract according to claim 1, wherein the extracting is carried out at a temperature in a range of 20° C. to 60° C. for a period of 8 hours to 20 hours.

8. The extract according to claim 1, wherein during the extracting of the crushed vanilla beans, the extraction solvent or the extraction solvent mixture is consecutively renewed at least twice to a maximum of five times, and the raw extracts obtained in each extraction are combined.

9. The extract according to claim 1, wherein the protective solvent is a solvent with a boiling point which is at least 20° C. higher than the boiling point of the extraction solvent or of the at least one organic extraction solvent in the extraction solvent mixture.

10. The extract according to claim 1, wherein the protective solvent is added to the raw extract in a ratio to the crushed vanilla beans in a range of 10:1 (w/w) to 1:10 (w/w).

11. The extract according to claim 10, wherein the protective solvent is added to the raw extract in a ratio to the crushed vanilla beans in a range of 1:1 (w/w) to 1:4 (w/w).

12. The extract according to claim 1, wherein the extraction solvent or the extraction solvent mixture is evaporated at a temperature in a range of 20° C. to 60° C. and under a vacuum in a range of 1 mbar to 500 mbar.

13. The extract according to claim 2, wherein the phase separation is carried out at a temperature in a range of 10° C. to 40° C. and for a period of 10 hours to 48 hours.

14. The ethanol-free vanilla extract according to claim 3, which has a lower content of ether compounds than an ethanol-vanilla extract of the same concentration, according to the same extraction method and from the same fermented vanilla beans, which has a vanillin methyl ether content (indicated as area percentage), which is at least 70%, lower, relative to a vanillin ethyl ether content (expressed as a percentage by area) of an ethanol-vanilla extract of the same concentration, by the same extraction method and from the same fermented vanilla beans, determined by SBSE-GCMS; and/or guaiacol in an amount (expressed as area percentage) which is at least 200% greater than the amount of guaiacol (expressed as area percentage) in an ethanol-vanilla extract of the same concentration, by the same extraction method and from the same fermented vanilla beans, determined by SBSE-GCMS; and/or p-hydroxybenzaldehyde in an amount (expressed as area percent) at least 300% greater than the amount of p-hydroxybenzaldehyde (expressed as area percent) in an ethanol-vanilla extract at the same concentration, by the same extraction method and from the same fermented vanilla beans, determined by SBSE-GCMS.

15. The extract according to claim 3, in which a quantitative ratio of guaiacol contained in the ethanol-free vanilla extract to vanillin contained in the ethanol-free vanilla extract is in a range of 1 to 0.001 and/or in which a quantitative ratio of p-hydroxybenzaldehyde contained in the ethanol-free vanilla extract to vanillin contained in the ethanol-free vanilla extract is in a range of 0.001 to 0.1, the ratios determined by means of GCMS peak areas in relation to an internal standard 2-nonanol.

16. The extract according to claim 3, in which a quantitative ratio of acetal compounds contained in the ethanol-free vanilla extract to vanillin contained in the ethanol-free vanilla extract is in a range of 0.0005 to 0.01 and/or in which a quantitative ratio of ether compounds contained in the ethanol-free vanilla extract to vanillin contained in the ethanol-free vanilla extract is in a range of 0.001 to 0.1, the ratios being determined by means of GCMS peak areas in relation to an internal standard 2-nonanol.

17. The extract according to claim 3, which is free of waxes and fats in the group consisting of fatty acids, their glycerides and fatty alcohol esters.

18. A method of producing an article selected from a foodstuff, semi-luxury food, beverage product, semi-finished product, hygiene product, cosmetic or pharmaceutical product, tobacco product or product for animal feed comprising including the ethanol-free vanilla extract according to claim 3 in the article.

19. A foodstuff, luxury food, beverage product, semi-finished product, hygiene product, cosmetic or pharmaceutical product, tobacco product, or product for animal nutrition, comprising the ethanol-free vanilla extract according to claim 3, and wherein the foodstuff is selected from the group consisting of: dairy products, sweets, food supplements, dietary foods and food surrogates.

* * * * *